(12) United States Patent
Vesey

(10) Patent No.: US 7,098,042 B2
(45) Date of Patent: Aug. 29, 2006

(54) INTERNAL QUALITY CONTROL

(75) Inventor: Graham Vesey, Gladesville (AU)

(73) Assignee: BTF PTY Ltd., Fairlight (AU)

( * ) Notice: Subject to any disclaimer, the term of this patent is extended or adjusted under 35 U.S.C. 154(b) by 139 days.

(21) Appl. No.: 10/739,315

(22) Filed: Dec. 19, 2003

(65) Prior Publication Data

US 2004/0180330 A1    Sep. 16, 2004

Related U.S. Application Data

(62) Division of application No. 09/656,018, filed on Sep. 5, 2000, now abandoned.

(60) Provisional application No. 60/152,084, filed on Sep. 2, 1999.

(51) Int. Cl.
*G01N 33/533* (2006.01)
*G01N 37/00* (2006.01)

(52) U.S. Cl. .................. 436/546; 436/560; 436/63; 436/325; 435/7.1; 435/7.2; 435/7.92

(58) Field of Classification Search ............. 435/7.1, 435/7.2, 7.92; 436/63, 518, 546, 56, 325
See application file for complete search history.

(56) References Cited

U.S. PATENT DOCUMENTS

| | | | |
|---|---|---|---|
| 5,073,497 A | 12/1991 | Schwartz | 436/8 |
| 5,545,535 A | 8/1996 | Roth et al. | 435/34 |
| 5,573,909 A | 11/1996 | Singer et al. | 435/6 |
| 5,723,218 A | 3/1998 | Haughland et al. | 428/402 |
| 5,750,330 A * | 5/1998 | Tometsko et al. | 435/2 |
| 5,786,219 A | 7/1998 | Zhang et al. | 436/523 |
| 6,004,536 A | 12/1999 | Leung et al. | 424/9.6 |
| 6,225,046 B1 | 5/2001 | Vesey | 435/5 |
| 6,228,574 B1 | 5/2001 | Rotman | 435/4 |
| 6,254,869 B1 | 7/2001 | Petersen | 424/191.1 |

FOREIGN PATENT DOCUMENTS

WO    WO 97/08204    3/1997

OTHER PUBLICATIONS

European Search Report for Application No. 00945465.3-2404-AU0000896, 4 pages, European Patent Office, Munich, Germany (mailed Mar. 3, 2004).
Vesey, G., et al., "Application of Flow Cytometric Methods for the Routine Detection of *Cryptosporidium* and *Giardia* in Water," *Cytometry* 16:1-6, (May 1994).
Nieminski, E.C., et al., "Comparison of Two Methods for Detection of *Giardia* Cysts and *Cryptosporidium* Oocysts in Water,"*Appl. Environ. Microbiol.* 61:1714-1719, (May 1995).
Hashimoto, A., et al., "Prevalence of *Cryptosporidium* oocysts and *Giardia* cysts in the drinking water supply in Japan," *Water Res.* 36:519-526, (Feb. 2002).

* cited by examiner

*Primary Examiner*—Long V. Le
*Assistant Examiner*—Jacob Cheu
(74) *Attorney, Agent, or Firm*—Cooley Godward LLP

(57) ABSTRACT

This invention relates to the field of internal quality control in diagnostic analysis, particularly in the analysis of microorganisms or other small particles, such as the detection of bacteria, protozoa, yeast, fungi, viruses, prions and the like, in water or other potable fluids, food, blood, urine, faeces, cerebro spinal fluid, and the like.

20 Claims, No Drawings

INTERNAL QUALITY CONTROL

CROSS REFERENCE TO RELATED APPLICATIONS

This is a divisional of U.S. application Ser. No. 09/656,018, filed Sep. 5, 2000 now abandoned which claims the benefit of U.S. Provisional application No. 60/152,084, filed Sep. 2, 1999, all of which are herein incorporated by reference.

BACKGROUND OF THE INVENTION

Water is routinely tested for the presence of *Cryptosporidium* and *Giardia*. Detection relies on immunofluorescence techniques to stain cysts and oocysts with a green fluorescent dye. The stained sample is examined using epifluorescent microscopy and the number of green fluorescing cysts and oocysts recorded.

The methodology involves numerous processes is which cysts and oocysts can be lost. It is, therefore, important to perform stringent quality control to monitor the performance of the methodology. At present, quality control is an external process that involves analysing a standard that contains a known number of cysts and oocysts. Such a quality control test is typically performed after analysing 10 or 20 samples. This external quality control is far from ideal. Losses of cysts and oocysts can very greatly between different samples. Some samples may be unsuitable for analysis. Furthermore, if the quality control result is poor then all results from the 10 or 20 samples must be discarded.

The same situation applies to diagnostic analysis in a wide variety of fields, where an external quality control is subject to the relevant diagnostic analysis being applied as a measure of performance/accuracy.

A need accordingly exists for accurate, convenient, cost-effective, and repeatable quality control in diagnostic analysis, which is currently not met by the prior art.

SUMMARY OF INVENTION

In accordance with a first aspect of this invention there is provided a diagnostic internal control method comprising providing a population of bioparticles, modifying the bioparticles to permanently and detectably tag each bioparticle to give tagged bioparticles, forming an internal quality control sample of a defined quanta of tagged bioparticles in a defined volume of carrier, adding the control sample to an assay sample for the detection of the same bioparticles, carrying out said assay, and thereafter determining the precise number of tagged bioparticles detected in the assay which on comparison with the quanta of added tagged bioparticles provides a determination of assay accuracy.

In accordance with a further aspect of this invention there is provided a method for providing an internal quality control in the analysis of bioparticles in potable fluids, which method comprises providing a sample of the bioparticles, subjecting the sample to detectable tagging, forming an internal control sample of a defined quanta of tagged bioparticles in a determined volume, adding said internal control sample to a test sample and subjecting the sample to analysis and determining the proportion of tagged bioparticles within the sample, wherein comparing the number of detected tagged test bioparticles compared with the known quanta of tagged bioparticles added to the sample provides a measure of assay accuracy and gives actual numbers allowing for losses in performing the assay.

In accordance with a further aspect of this invention there is provided an internal quality control standard which comprises a predetermined quanta of bioparticles, said bioparticles being of the type subject to routine analysis, said predetermined quanta of bioparticles being tagged with a detectable tag, and provided in a carrier of defined volume.

DETAILED DESCRIPTION OF THE INVENTION

The accuracy of diagnostic assays is critical to their performance as a tool in modern analysis. Plainly, an assay which does not give accurate results is of no real benefit as it may understate or overstate the presence of the specific entity being measured. Incorrect analysis may give rise to inappropriate decisions being made and these may have significant deleterious effects.

This invention is concerned with internal quality control, that is providing internal standards of tagged bioparticles which are added to a sample and subject to routine analysis, whereafter the number of tagged bioparticles in the sample, when compared with the known number of bioparticles added to the sample, is a direct measure of assay accuracy.

In accordance with a first aspect of this invention there is provided a diagnostic internal control method comprising providing a population of bioparticles, modifying the bioparticles to permanently and detectably tag each bioparticle to give tagged bioparticles, forming an internal quality control sample of a defined quanta of tagged bioparticles in a defined volume of carrier, adding the control sample to an assay sample for the detection of the same bioparticles, carrying out said assay, and thereafter determining the absolute number of tagged bioparticles detected in the essay which on comparison with the quanta of added tagged bioparticles provides a determination of assay accuracy.

The bioparticles may be a microorganism, for example selected from a bacteria, fungus, yeast or virus, or may be a single or multi-cellular protozoa, a prion or other bioparticle. Examples of such bioparticles include *Cryptosporidium, Giardia, Cyclospora, Toxoplasma, Eimeria, Legionella, Samonella, Leptospirosis, Escherichia, Saccharomyces, Clostridium, Vibrio, Pseudomonas, Anthrax,* blood cells, HIV, Norwalk virus, herpes simplex virus.

The assay sample for the detection of bioparticles, may be water or another potable fluid such as fruit juice, wine, beer, milk, cider or the like. The sample may be a food, such as poultry, beef, eggs, cheese, preserved meats such as salami or ham and the like. The sample may be in the form of blood, cerebro spinal fluid, urine, tissue extracts, faeces, and the like.

Bioparticles which comprise the control bioparticles are detectably tagged with a tag which alters the chemical and/or physical properties of the bioparticle in a manner which is readily detectable. An example of ready detectability is via microscopic analysis, where tags such as fluorophores may be used. When shone with light at an appropriate wavelength, fluorophores fluoresce thus identifying bioparticles tagged with the fluorophores. Non-tagged bioparticles do not fluoresce under such conditions. Other readily detectable tags which effect the physical and/or chemical properties of labelled bioparticles, such as density, shape or appearance include colloidal compounds such as colloidal gold, labelling with electron dense agents such as ferritin or other iron or heavy metal compounds/complexes and the like. Other tags which may be used include radiolabelling using a radioactive isotope, for example which tags cell surface protein, lipids or carbohydrates or internal such species, and modification of the DNA or RNA to alter the chemical and/or physical properties of the bioparticle. The latter may involve incorporation of a gene that causes luminescence (Catrin et al., 1999), fluorescence (Nobuhide Doi & Hiroshi Yanagawa, 1999) or other well established gene expression systems such as antibiotic resistance, chemical tolerance, antigen expression, enzyme expression or a change in metabolic activity.

Detectable tags may tag cell surface proteins, lipids, glycolipids, and/or carbohydrate, or internal such species within the bioparticle. Where tags bind permanently to cell surface or intracellular proteins, lipids and/or carbohydrates various advantages arise. For example, such cells do not need to be permobilised or changed in any physical way for labelling to occur, the tagging is permanent, and damage or disruption of cells will not cause the signal from the detectable tag to be lost.

DNA or RNA within a bioparticle may be tagged in a permanent or non-permanent manner, for example using nucleic acid reactive fluorochromes which form a permanent bond with DNA or RNA, or DNA/RNA intercollating fluorochromes which do not form a permanent bond with DNA or RNA. DNA/RNA tagging may not be as advantageous as other forms of tagging mentioned above due to DNA/RNA turnover/degradation which may cause the tag to be lost or diminished in detectable signal.

Methods for detectably tagging or labelling bioparticles, such as microorganisms, yeast cells, viruses and the like are well established, see for example Gröndahl et al., 1997 and Chaka et al., 1995. Fluorescently stained yeast and bacteria are an item of commerce, being sold by various companies, including Molecular Probes Inc of Eugene, USA. By way of example, cells to be labelled with a fluorescent marker may simply be added to a solution of the fluorophore such that proteins or other species on the cell surface, or on the inside of the cell, are fluorescently labelled. Fluorochromes are generally provided with one or more functional groups which allow coupling for example to protein functional groups such as the $\epsilon$-amino group of lysine.

In like manner, colloidal agents, electron dense agents and the like generally contain one or more reactive groups or are derivatised to contain one or more reactive groups to allow labelling, for example with proteinaceous functional groups, such as the $\epsilon$-amino group of lysine, or the carboxylic acid functionality of glutamic acid.

The DNA or RNA of a microorganism may be altered to include a DNA sequence which produces a physical or chemical change in the microorganism, detectable for example by change of shape, density, morphological appearance and the like using established molecular biology techniques a are known in the art (see, for example, Catrin et al., 1999; Nobuhide Doi & Hiroshi Yanagawa, 1999).

Where in a routine assay different types of bioparticles are analysed, the control sample may contain a predetermined number of each type of bioparticle, with each type of bioparticle being tagged in a manner which allows ready identification of each type of tagged bioparticle. An example would be to tag each type of bioparticle with a different type of fluorescently active agent. For example a wide variety of dyes are commercially available which fluoresce green, red, yellow, orange or blue, such as Fluorescein or Rhodamine (Haugland 1998).

Bioproperties are inactivated either prior to or after tagging to provide stability carried out by established techniques such as X-ray inactivation, snap freezing, chemical inactivation and the like. The inactivation does not effect the chemical or physical properties of the bioparticle, such that in assay it behaves in the same manner as bioparticles being tested in assay conditions.

Tagged bioparticles are detected within the process of analysis, hence the control is an internal control. The type of routine analysis depends on the analysis system used in the specific diagnostic assay being carried out. By way of example, water quality may be determined by microscopic analysis of a water sample under high magnification where the different types of bioparticles, such as microorgansims and protozoans, can be identified.

Other diagnostic assays may involve flow cytometry where cells can be readily sorted according to their physical properties (Shapiro, 1995). The assay of bioparticles, such as microorganisms, in water or other potable fluids, in food analysis, and in analysis of biological fluids such as blood, sputum, cerebro spinal fluid, faecal material and the like, may be conducted by way of microscopic analysis, flow cytometry, cytometry, laser scanning cytometry, confocal microscopy or other well established analytical techniques as routinely used in water and feed analysis, medical diagnostic tests, cell culture, tissue culture infectivity and animal infectivity analysis. Also, immunological detection methods such as enzyme linked immunoabsorbant assays (ELISA), colour-metric detection and imunofluorescence, or nucleic acid detection methods such as DNA or RNA probe hybridisation, fluorescence in-situ hybridisation (FISH) or polymerase chain reaction (PCR) may be used.

Whatever type of assay is carried out for the detection of bioparticles, the control sample of a predetermined quanta of bioparticles is added to the assay, the assay is carried out, and the determination of the proportion of tagged bioparticles so detected in the assay sample is made and compared with the predetermined number of tagged bioparticles added, as a measure of assay accuracy. This may be referred to as enumeration, a characteristic feature of this invention, where the precise number of tagged bioparticles in a control sample is known/predetermined, and on addition of the control sample to an assay, are precisely or absolutely determined as a measure of assay efficiency. The measure of assay efficiency is then used to calculate the number of test organisms present in the sample. Particularly, the number of tagged bioparticles detected when compared with the quanta added to the assay gives a percentage recovery, for example if 10 tagged bioparticles are added to an assay for the same bioparticle and 8 tagged bioparticles are detected on analysis the percentage recovery is 80%. This is a direct measure of the percentage recovery/detection-of untagged particles in the assay.

In accordance with a further aspect of this invention there is provided a method for providing an internal quality control in the analysis of bioparticles in potable fluids, which method comprises providing a sample of bioparticles, subjecting the sample to detectable tagging, forming an internal control sample of a defined quanta of tagged bioparticles in a determined volume, adding said internal control sample to a test sample and subjecting the sample to analysis and determining the proportion of tagged bioparticles within the sample, wherein comparing the number of detected tagged test bioparticles compared with the known quanta of tagged bioparticles added to the sample provides a measure of assay accuracy.

Preferably, the potable fluid is water, and examples of bioparticles which may be detected include *Cryptosporidium* and *Giardia*.

In a further aspect of this invention there is provided an internal quality control standard which comprises a predetermined quanta of bioparticles, said bioparticles being of the type subject to routine analysis, said predetermined quanta of bioparticles being tagged with the detectable tag, and provided in a carrier of defined volume.

Bioparticles which are tagged as previously described may be formed into a predetermined number in a predetermined volume of carrier, for example by way of flow cytometry where cells are separated based on their physical properties (Shapiro, 1995; Vesey et al., 1994), or by other standard techniques in the art.

The tagged bioparticles in defined quanta and volume may be provided in a container which allows for ready addition of said tagged bioparticles to an assay sample.

The present invention has wide applicability in testing samples for the presence of bioparticles, for example microorganisms. One specific area of importance is in quality control in relation to water testing. Potable water is generally tested for the presence of microorganisms, in particular, the presence of the organisms *Cryptosporidium* and *Giardia*. Detection relies on immunofluorescence techniques to stain cysts and oocysts with a green fluorescent dye. The stained sample is examined using epifluorescent microscopy and the number of green fluorescing cysts and oocysts recorded. As mentioned above it is important to perform stringent quality control procedures to monitor the performance of the methodology. The present invention enables monitoring the quality of analysis of every sample which is analysed. Water-samples may have added to them known numbers of tagged cysts and oocysts, for example which have been tagged with a blue fluorescent dye. When the example is examined for green fluorescing cysts and oocysts, further examination is performed to determine if the cysts or oocysts are an internal standard. The cysts and oocysts may be simply examined to determine if they are fluorescing blue as well as green. Any cysts or oocysts detected at fluoresce green but not blue are not an internal standard. In this approach, various fluorescent dyes may be used which distinguish the labelled microorganisms. Other labelling techniques as described above may of course be utilised.

In the water quality area, it is convenient to inactive cysts and oocysts with gamma radiation prior to conjugation with a fluorescent dye or other labelling agent. The organisms which are tagged are generally inactivated as discussed above. Flow cytometry is generally used to accurately dispense a known number of labelled cysts and oocysts into a test tube. The test tubes may be sealed and irradiated with, for example, gamma irradiation to sterilise the sample and increase shelf life. The sample may be stored at low temperature, for example 4° C. until used in a standard assay for water quality.

The invention described herein allows the accurate enumeration of the internal control bioparticles, for example control cells. This enumeration which is plainly distinct from the prior art is essential as it is critical that the precise or absolute number of test organisms in a sample be measured to enable an assessment of assay accuracy.

As previously mentioned, this invention has wide applicability in the detection of microorganisms or other bioparticles, for example, the detection of bacteria, protozoa, yeast, fungi or viruses in food, water or other potable liquids, blood, urine, faeces, food etc.

This invention will now be described by reference to the following non-limiting examples.

EXAMPLE 1

*Cryptosporidium* and *Giardia*

*Cryptosporidium parvum* oocysts are purified from pooled faeces of naturally infected neonatal calves in Sydney. Faecal samples are centrifuged (2000 g, 10 min) and resuspended in water twice and then resuspended in 5 volumes of 1% (w/w) $NaHCO_3$. Fatty substances are then extracted twice with 1 volume of ether, followed by centrifugation (2000 g for 10 min). Pellets are resuspended in water and filtered through a layer of pre-wetted non-adsorbent cotton wool. The eluate is then overlaid onto 10 volumes of 55% (w/v) sucrose solution and centrifuged (2000 g for 20 min). Oocysts are collected from the sucrose interface and the sucrose flotation step repeated until no visible contaminating material could be detected. Purified oocysts are surface sterilised with ice cold 70% (v/v) ethanol for 30 min, washed once in phosphate buffered saline (150 m mol $1^{-1}$ NaCl, 15 m mol $1^{-1}$ $KH_2PO_4$, 20 m mol $1^{-1}$ $Na_2HPO_4$, 27 m mol $1^{31\ 1}$ KCl, pH 7.4) (PBS), and diluted in PBS to a concentration of approximately $1\times10^7$ oocysts $ml^{-1}$ and stored at 4° C.

*Giardia lamblia* cysts were purchased from Waterborne Inc (New Orleans, USA).

Conjugation of Fluorochromes to Cysts and Oocysts

Some samples of cysts and oocysts are frozen (−80° C.) to disrupt the cyst and oocyst walls prior to conjugation.

Aliquots (200 µl) of cysts and oocysts (containing approximately $1\times10^7$ are centrifuged at 12000 g for 2 minutes and the supernatant removed and discarded. Cysts and oocysts are resuspended in 0.1M sodium bicarbonate pH 8.3. This washing procedure was repeated twice.

The blue fluorochrome Alexa 350 carboxylic acid, succinimidyl ester (Alexa 350—Molecular Probes, Eugene, USA) is dissolved in dimethylsulfoxide (DMNSO) at a concentration of 1 mg per ml.

Aliquots (10 µl) of the fluorochrome/DMSO mixture are added to 200 µl of the cysts and oocyst suspensions. Samples are mixed thoroughly and incubated at room temperature for 30 minutes. Samples are then centrifuged at 12000 g for 2 minutes and the supernatant removed and discarded. Cysts and oocysts are resuspended in 0.1M sodium bicarbonate. This washing procedure is repeated twice.

Aliquoting

Labelled cysts and oocysts are accurately dispensed into 6 ml plastic test tubes using flow cytometry. A Becton Dickinson FACScalibur flow cytometer is used to analyse labeled cysts and oocysts. Fluorescence and or light scatter properties of cysts or oocysts are defined and these properties used to sort 100 labeled cysts and oocysts from a sample of labeled cysts and oocysts. Sorted cysts and oocysts are dispensed into a test tube.

It is important that all cysts and oocysts that are sorted are labeled. If an unlabelled cyst or oocyst ends up in the sample then false positive results would occur.

Quality control is performed to ensure that accurate numbers of cysts and oocysts are dispensed. In this regard a proportion of test tubes are analysed using microscopy or flow cytometry to enumerate cysts and oocysts. Test tubes are weighed and tubes of and outlying weight would be discarded.

Seeding Water Samples with Control Material

Samples of water are either collected in containers and shipped to a laboratory for concentration or samples concentrated at the sampling location. Samples that are shipped to laboratories for concentration normally range in volume from 10 to 100 litres. The sample is seeded with the control sample using the following seeding method:
1) Add 2 ml of 0.05% (v/v) tween 80 to the tube of control material.
2) Replace cap and shake vigorously.
3) Remove cap and pour control material into sample.
4) Add 3 ml of 0.05% (v/v) tween 80 to the control material tube.
5) Replace cap and shake vigorously.
6) Remove cap and pour control material into sample.
Repeat steps 4, 5 and 6.

The sample is concentrated using conventional methods such as membrane filtration, cartridge filtration, pleated membrane cartridge filtration, flocculation or vortex flow filtration (Anon, 1999; Vesey et al., 1994).

If the water sample is concentrated at the sample site then a portable concentration method such as cartridge filtration is employed. The filter cartridge should be seeded with the control material before concentration of the sample. The seeding method described above is suitable for seeding the filter cartridge.

Manufacturers of cartridge filters may seed filters during the manufacturing process.

Filters that have been used to concentrate water samples are returned to the analysis laboratory and the particulate material collected within the filter is eluted and further concentrated Analysis Concentrated samples are treated to remove contaminating particles such as algae and mineral particles. Methods such as floatation, immunomagnetic separation (IMS) and flow cytometry are roughly used for purifying cysts and oocysts from water concentrates (Vesey et al., 1994; Anon, 1999).

Purified samples are then transferred to a glass microscope slide or onto a small (13 mm) membrane filter. The slide or the membrane is stained with fluorescein isothiocyanate (FITC) stained monoclonal antibodies, incubated and washed and examined using epifluorescence microscopy (Vesey et al., 1993; Anon, 1999), for example using a Nikon Optiphot2 epifluorescence microscope fitted with ×12 eyepieces and a ×20 objective (Fluor20) for examination of samples. A DM510 filter block is used for the examination of fluorochrome fluorescein isothiocyanate FITC labelled samples. The membrane or slide would be carefully scanned and the cysts and oocysts detected.

When a green fluorescing cysts or oocysts is detected it would be examined using different optical filters to determine if it was fluorescing blue thus identifying it as a control cyst or oocyst. A DM450 filter block is used for the detection of the blue fluorescence from Alexa 350 labeled control cysts and oocysts.

Once the entire membrane has been scanned the total number of cysts and oocysts detected in the sample is compared with the number of cysts and oocysts detected that fluoresce blue. These figures are then used to calculate the recovery efficiency and the actual number of cysts and oocysts present in the water sample. In one example, the sample is seeded with 100 blue control cysts and 100 blue control oocysts. Analysis of the sample results in the detection of 50 blue cysts and 30 non-blue cysts and 50 blue oocysts and 10 non-blue oocysts. The recovery efficiency of the analysis is 50% for both cysts and oocysts (seeded with 100 and only 50 detected). The sample, therefore, contained 60 cysts and 20 oocysts.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

REFERENCES

Anon. Method 1623: *Cryptosporidium* and *Giardia* in Water by Filtration/IMS/FA. United States Office of Water EPA-821-R-99-006. Environmental Protection Agency Washington, DC 20460 April 1999.

Yeomans, C.; Porteous, F.; Paterson, E.; Meharg, A and Kiliham, K., 1999. Assessment of lux-marked *Pseudomonas fluorescens* for reporting on organic carbon compounds. *FEMS Microbiology Letters*, Volume 176, Issue 1, Pages 79–83

Gröndahl, G.; Johannisson, A. and Jensen-Waern. M., 1997. Opsonic effect of equine plasma from different donors. *Veterinary Microbiology*, Volume 56, Issue 3–4, Pages 227–235

Doi. N. and Yanagawa, H., 1999. Design of generic biosensors based on green fluorescent proteins with allosteric sites by directed evolution, *FEBS Letters*, Volume 453, Issue 3, Pages 305–307

Chaka, W.; Scharringa, J.; Verheul, A. F. M.; Verhoef, J.; Van Strijp, A. G.; Hoepelman, I. M., 1995. Quantitative analysis of phagocytosis and killing of cryptococcus neoformans by human peripheral blood mononuclear cells by flow cytometry, *Clinical and Diagnostic Laboratory Immunology*, Volume 2, Issue 6, Pages 753–759

Haugland, R. P., 1998. *Handbook of fluorescent probes*. Molecular Probes, Eugene, USA (www.probes.com)

Shapiro, H. M., 1995. *A practical guide to flow cytometry*, third edition. A. R. Liss, New York.

Vesey, G., Hutton, P. E., Champion, A. C., Ashbolt, N. J., Williams, K. L., Warton, A., and Veal, D. A., 1994. Application of flow cytometric methods for the routine detection of *Cryptosporidium* and *Giardia* in water. *Cytometry*, 16, 1–6.

Vesey. G.; Narai, J; Ashbolt, N., Williams, K. L. and Veal, D. A. 1994. Detection of specific microorganisms in environmental samples using flow cytometry. In: *Methods in Cell Biology, Volume 42—Flow Cytometry Second Edition*. ed. Darzynkiewicz, Z., Robinson; J. P. and Crissman, H. A. pp. 489–522, Academic Press Inc., New York.

The claims defining the invention are as follows:

1. A method for calibrating or determining accuracy or efficiency of a microbial assay, comprising:
   (a) providing an internal quality control standard to a sample to be assayed and suspected of containing a microorganism type, the standard comprising a defined quantum of a modified form of the microorganism type, wherein the modified microorganism comprises a detectable tag such that the modified microorganism can be differentiated from the corresponding unmodified microorganism in a sample being assayed;
   (b) carrying out an assay on the sample so as to detect and determine the number of unmodified microorganisms and the number of modified microorganisms present in the sample; and
   (c) comparing the number of modified microorganisms detected by the assay with the defined quantum of modified microorganisms provided to the sample so as to calibrate or determine the efficiency of the assay, wherein the number of detected modified microorganisms is compared with the defined quantum of modified microorganism added to the sample and the comparison is indicative of the efficiency of the assay for the microorganism.

2. The method according to claim 1 wherein the internal quality control standard comprises at least two types of modified microorganism so that the assay can be calibrated for each microorganism type.

3. The method according to claim 1 wherein the microorganism is selected from the group consisting of bacterium, protozoa, yeast, fungi, and virus.

4. The method according to claim 3 wherein the microorganism is selected from the group consisting of *Cryptosporidium, Giardia, Cyclospora, Toxoplasma, Eimeria, Legionella, Samonella, Leptospirosis, Escherichia, Saccharomyces, Clostridium, Vibrio, Pseudomonas*, human immunodeficiency virus, Norwalk virus, and herpes simplex virus.

5. The method according to claim 4 wherein the microorganism is *Cryptosporidium*.

6. The method according to claim 4 wherein the microorganism is *Giardia*.

7. The method according to claim 1 wherein the modified microorganism is inactivated such that the microorganism is not viable.

8. The method according to claim 1 wherein the modified microorganism comprises a detectable tag attached to surface molecules on the microorganism or resides inside the microorganism.

9. The method according to claim 8 wherein the microorganism is modified by chemical treatment or by genetic manipulation to provide the detectable tag.

10. The method according to claim 8 wherein the modified microorganism comprises a detectable tag attached to its outer surface.

11. The method according to claim 1 wherein the detectable tag alters a chemical property of the microorganism, alters a physical property of the microorganism, or alters both a chemical property and a physical property of the microorganism in a manner which allows the modified microorganism to be differentiated from a corresponding unmodified microorganism present in a sample being assayed.

12. The method according to claim 1 wherein the detectable tag is a fluorescent tag.

13. The method according to claim 12 wherein the fluorescent tag is a red, blue or green fluorochrome.

14. The method according to claim 1 wherein the predetermined quantum of modified microorganisms is from 1 to 100000.

15. The method according to claim 14 wherein the predetermined quantum of modified microorganism is about 100.

16. The method according to claim 1 wherein the predetermined quantum of modified microorganism is in a diluent of defined volume.

17. The method according to claim 16 wherein the defined volume is up to about 10 ml.

18. The method according to claim 1 wherein the assay is for detection of microorganisms in samples selected from the group consisting of water or other potable liquid, food, blood, sputum, mucous, urine and cerebrospinal fluid.

19. The method according to claim 18 wherein the potable fluid is fruit juice, wine, beer, milk, or cider, and the food is poultry, beef, eggs, cheese, or preserved meats.

20. The method according to claim 18 wherein the assay for detection of microorganisms in water is by microscopy.

* * * * *